(12) United States Patent
Gravesen et al.

(10) Patent No.: US 8,230,744 B2
(45) Date of Patent: Jul. 31, 2012

(54) LOW-DEAD VOLUME MICROFLUIDIC CIRCUIT AND METHODS

(75) Inventors: Peter Gravesen, Nordborg (DK); Heiko Arndt, Flensborg (DE)

(73) Assignee: CeQur SA, Horw (CH)

( * ) Notice: Subject to any disclaimer, the term of this patent is extended or adjusted under 35 U.S.C. 154(b) by 458 days.

(21) Appl. No.: 12/436,365

(22) Filed: May 6, 2009

(65) Prior Publication Data

US 2010/0281990 A1    Nov. 11, 2010

(51) Int. Cl.
*G01L 7/08* (2006.01)

(52) U.S. Cl. .......................................................... 73/715

(58) Field of Classification Search .................. 73/715, 73/40.5; 600/347
See application file for complete search history.

(56) References Cited

U.S. PATENT DOCUMENTS

| | | | |
|---|---|---|---|
| 3,144,879 A | 8/1964 | Baumann |
| 3,722,756 A | 3/1973 | Cramer, Jr. |
| 3,880,151 A | 4/1975 | Nilsson et al. |
| 3,904,111 A | 9/1975 | Petersson |
| 3,977,600 A | 8/1976 | Sheets, Jr. |
| 4,398,542 A | 8/1983 | Cunningham et al. |
| 4,759,883 A | 7/1988 | Woody et al. |
| 5,176,358 A | 1/1993 | Bonne et al. |
| 5,271,724 A | 12/1993 | van Lintel et al. |
| 5,306,257 A | 4/1994 | Zdeb |
| 5,360,411 A | 11/1994 | Mimura et al. |
| 5,810,325 A | 9/1998 | Carr |
| 5,839,467 A | 11/1998 | Saaski et al. |
| 6,056,269 A | 5/2000 | Johnson et al. |
| 6,068,751 A | 5/2000 | Neukermans |
| 6,227,824 B1 | 5/2001 | Stehr et al. |
| 6,589,229 B1 | 7/2003 | Connelly et al. |
| 6,644,944 B2 | 11/2003 | Karp |
| 6,713,151 B1 | 3/2004 | Dean et al. |
| 6,716,193 B1 | 4/2004 | Neftel et al. |
| 6,852,094 B2 | 2/2005 | Beck et al. |
| 6,919,046 B2 | 7/2005 | O'Connor et al. |
| 6,948,373 B2 | 9/2005 | Imai et al. |
| 7,094,345 B2 | 8/2006 | Gilbert et al. |

(Continued)

FOREIGN PATENT DOCUMENTS

DE          10325110          1/2005

(Continued)

OTHER PUBLICATIONS

U.S. Appl. No. 12/436,360 Heiko Arndt filed Nov. 11, 2010.*

(Continued)

*Primary Examiner* — Jewel V Thompson
(74) *Attorney, Agent, or Firm* — Goodwin Procter LLP

(57) ABSTRACT

A method is described for reducing a dead volume of a microfluidic circuit that includes, in one embodiment, a reservoir, an outlet, and a microfluidic flowpath fluidly connecting the reservoir and the outlet. The method includes providing a microfluidic flow component between the reservoir and the outlet for performing a function and in fluidic communication with the microfluidic flowpath, wherein the microfluidic flow component includes a total volume including a working volume and a dead volume. The working volume is a volume necessary for the microfluidic flow component to perform the function and the dead volume is a volume unnecessary for the microfluidic flow component to perform the function. The method includes configuring at least one of the reservoir, the microfluidic flowpath, and the microfluidic flow component to reduce the dead volume, such that the working volume of the component is substantially the same as the total volume.

11 Claims, 7 Drawing Sheets

U.S. PATENT DOCUMENTS

| | | |
|---|---|---|
| 7,094,379 B2 | 8/2006 | Fouillet et al. |
| 7,143,787 B1 | 12/2006 | Bauerle et al. |
| 7,152,616 B2 | 12/2006 | Zucchelli et al. |
| 7,159,618 B2 | 1/2007 | Broyer et al. |
| 7,207,345 B2 | 4/2007 | Somerville et al. |
| 7,244,961 B2 | 7/2007 | Jovanovich et al. |
| 7,291,126 B2 | 11/2007 | Shekalim et al. |
| 2002/0087147 A1 | 7/2002 | Hooper et al. |
| 2003/0015682 A1 | 1/2003 | Killeen et al. |
| 2004/0104173 A1 | 6/2004 | Manach et al. |
| 2004/0209354 A1 | 10/2004 | Mathies et al. |
| 2004/0245102 A1 | 12/2004 | Gilbert et al. |
| 2005/0013732 A1 | 1/2005 | Battrell et al. |
| 2005/0045733 A1 | 3/2005 | Phipps |
| 2005/0205816 A1 | 9/2005 | Hayenga et al. |
| 2005/0255003 A1 | 11/2005 | Summersgill et al. |
| 2005/0266582 A1 | 12/2005 | Modlin et al. |
| 2006/0000238 A1 | 1/2006 | Griffin et al. |
| 2006/0011882 A1 | 1/2006 | Arndt et al. |
| 2006/0169702 A1 | 8/2006 | Shen et al. |
| 2006/0184121 A1 | 8/2006 | Brockman et al. |
| 2007/0003448 A1 | 1/2007 | Kanigan et al. |
| 2008/0029169 A1 | 2/2008 | Maerkl et al. |
| 2008/0234630 A1 | 9/2008 | Iddan et al. |
| 2008/0281276 A1 | 11/2008 | Shekalim |

FOREIGN PATENT DOCUMENTS

| | | |
|---|---|---|
| EP | 0 562 694 | 9/1993 |
| EP | 0 450 186 A1 | 2/1995 |
| EP | 0 737 483 | 10/1996 |
| EP | 1 254 676 A1 | 12/2003 |
| EP | 1818664 A1 | 8/2007 |
| GB | 2 197 691 | 5/1988 |
| GB | 2 031 558 | 3/2009 |
| JP | 07280050 | 10/1995 |
| JP | 08247327 | 9/1996 |
| WO | WO-2007125458 A2 | 11/2007 |
| WO | WO-2007140631 A1 | 12/2007 |
| WO | WO-2008075253 A1 | 6/2008 |
| WO | WO-2009050584 A2 | 4/2009 |

OTHER PUBLICATIONS

Invitation to Pay Additional Fees and, Where Applicable, Protest Fee mailed on Aug. 11, 2010 for Application No. PCT/IB2010/001211 and Attached Annex.

International Search Report and Written Opinion for Application No. PCT/IB10/001211 (20 pages), dated Feb. 25, 2011.

* cited by examiner

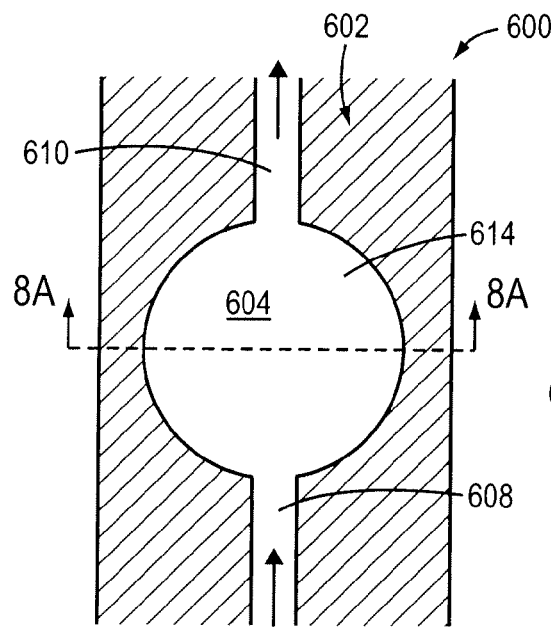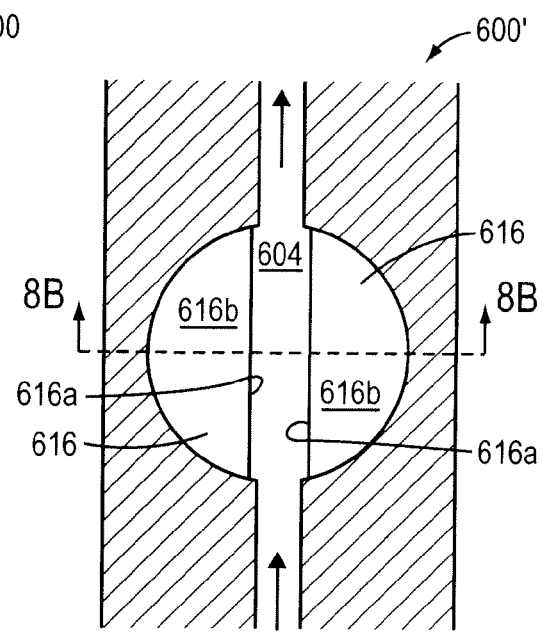
FIG. 7A  FIG. 7B
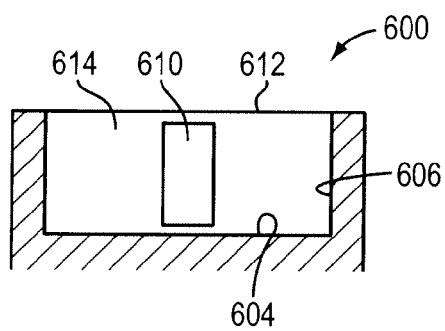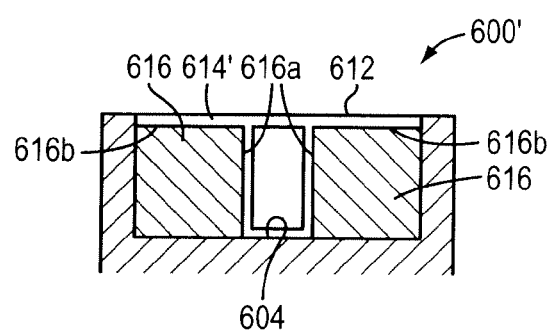
FIG. 8A  FIG. 8B

LOW-DEAD VOLUME MICROFLUIDIC CIRCUIT AND METHODS

FIELD OF THE INVENTION

This invention relates generally to systems and methods of reducing dead volume in a microfluidic circuit and, more specifically, to systems and methods of reducing the dead volume in components utilized within microfluidic circuits.

BACKGROUND

Microfluidic circuits are utilized in various personal medical devices (e.g., insulin infusion devices) to control delivery of medications or other fluids. In general, the volumetric flow rates within these circuits are very low, due to low dosing schedules, and to allow for accurate control of the medication being delivered. The low flow rates, however, can prevent the circuit from being quickly filled prior to utilizing the device, which can pose a significant inconvenience to the user. Additionally, any excess volume within the circuit results in medication that remains undelivered once a pressure source for the medication is terminated.

Lengthy fill times and undelivered medication are related to total volume within a microfluidic system. Each component (e.g., reservoirs or other chambers, valves, conduits or channels, pressure sensors, flow restrictors, etc.) of a system has an internal capacity for a volume of fluid. This capacity is defined, in part, by the internal dimensions, function, and configuration of the component, including moving components within the flowpath. Manufacturing methods and tolerances may affect the capacity, as well. While a particular component may only require a relatively small portion of the total internal volume to perform its function (this volume may be referred to as the "working volume"), access required for manufacturing the component may prevent minimizing the total volume. This excess volume (or "dead volume") over that of the working volume increases the total volume of the flow component and, subsequently, of the fluidic circuit of the delivery system.

SUMMARY OF THE INVENTION

In one aspect, the invention relates to a method for reducing a dead volume of a microfluidic circuit having a reservoir, an outlet, and a microfluidic flowpath fluidly connecting the reservoir and the outlet, the method including providing a microfluidic flow component located between the reservoir and the outlet for performing a function and in fluidic communication with the microfluidic flowpath. The microfluidic flow component includes a total volume having a working volume and a dead volume, wherein the working volume is a volume necessary for the microfluidic flow component to perform the function and the dead volume is a volume unnecessary for the microfluidic flow component to perform the function. The method includes configuring at least one of the reservoir, the microfluidic flowpath, and the microfluidic flow component to reduce the dead volume, such that the working volume is substantially the same as the total volume. In an embodiment, the configuring step results in the total volume being substantially the same as the working volume. In an embodiment, the microfluidic flow component is at least one of a flowpath, a valve, a constant-volume fluid chamber, and a pressure sensor.

In an embodiment of the above aspect, the microfluidic flow component is a constant-volume fluid chamber defining an internal chamber, a chamber inlet in fluidic communication with the internal chamber, and a chamber outlet in fluidic communication with the internal chamber, wherein the internal chamber is the total volume. The configuring step includes providing a volume reduction element within the internal chamber so as to define a reduced volume flow path from the chamber inlet to the chamber outlet. The reduced volume flow path substantially defines the working volume. In another aspect, the invention relates to a low-dead volume constant-volume fluid chamber manufactured in accordance with the method of the above embodiment. In an embodiment of the above aspect, the working volume is about 14% of the total volume.

In another embodiment, the microfluidic flow component is a valve, the valve having a housing defining a valve chamber therein. The valve chamber is defined at least in part by a sidewall and a valve seat, the valve seat having at least one of a base surface and a raised plateau defining a valve inlet and a plateau wall extending from the raised plateau to the base surface, the base surface defining a valve outlet, and a seal member having a surface corresponding substantially to the sidewall and the raised plateau. The configuring step includes providing a volume reduction element within the valve chamber, such that the seal member corresponds substantially to the base surface and the plateau wall. In another aspect, the invention relates to a low-dead volume valve manufactured in accordance with the method of the above embodiment. In an embodiment of the above aspect, the working volume is about 0% of the total volume.

In yet another embodiment, the microfluidic flow component is a variable-volume fluid chamber having a base surface, an inlet, and a separate outlet. The configuring step includes providing a flexible membrane, wherein the base surface and the membrane define a first volume when the membrane is proximate the base surface, and the base surface and the membrane define a second volume when the membrane is displaced by a fluid pressure away from the base surface. The membrane can be biased towards the base surface. In another aspect, the invention relates to a low-dead volume variable-volume fluid chamber manufactured in accordance with the method of the above embodiment. In an embodiment of the above aspect, the working volume is about 5% of the total volume.

In still another embodiment, the microfluidic flow component is a pressure sensor having a flexible membrane and a base surface disposed below the flexible membrane. A volume located between the flexible membrane and the base surface defines the total volume. The configuring step includes providing two raised structures disposed between the flexible membrane and the base surface. Top surfaces of the raised structures are proximate to, but not in contact with, the flexible membrane. Side surfaces of the raised structures intersect the base surface. The side surfaces of the raised structures, the base surface, and the flexible membrane at least partially define a flow channel. The flow channel defines the working volume. In another aspect, the invention relates to a low-dead volume pressure sensor manufactured in accordance with the method of the above embodiment. In an embodiment of the above aspect, the working volume is about 40% of the total volume.

BRIEF DESCRIPTION OF THE FIGURES

Other features and advantages of the present invention, as well as the invention itself, can be more fully understood from the following description of the various embodiments, when read together with the accompanying drawings, in which:

FIGS. 7A and 7B are schematic top views of an exemplary pressure sensor and a low-dead volume version of the same pressure sensor in accordance with one embodiment of the invention; and FIGS. 8A and 8B are schematic sectional views of the exemplary pressure sensor and the low-dead volume version of the same pressure sensor of FIGS. 7A and 7B.

DETAILED DESCRIPTION

Figure 1:
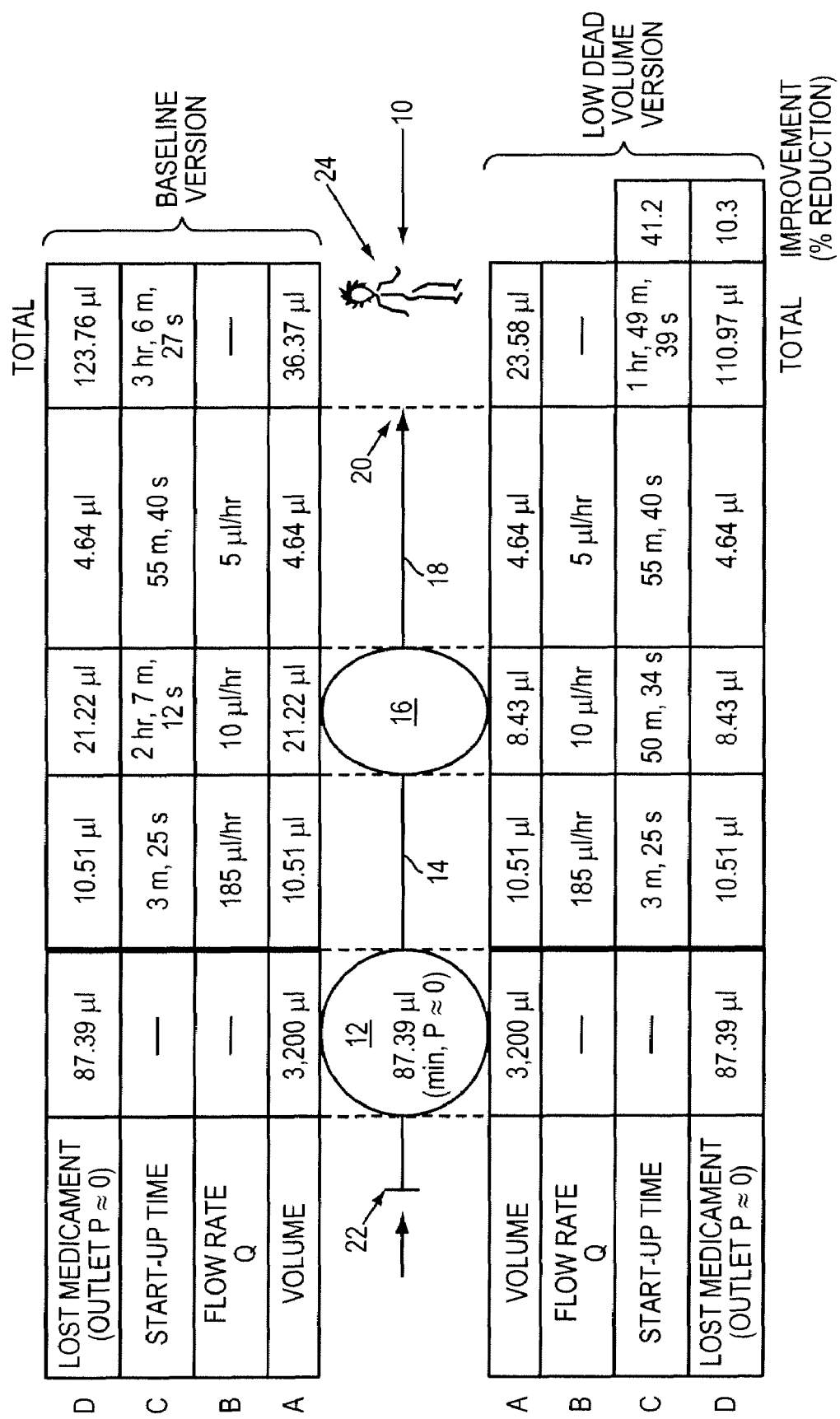
FIG. 1 is a schematic diagram and related time/volume tables of an exemplary infusion device microfluidic circuit.

Consider one embodiment of a microfluidic circuit 10 for delivering a fluid medication to a patient, as depicted in FIG. 1. The fluid delivery or flow components of this circuit 10 include, in series, an elastomer reservoir or bladder 12, a first channel 14, a pressure sensor 16, a second channel 18, and an outlet 20. The reservoir 12 is filled with medication via a one-way inlet valve 22. In this example, the microfluidic circuit 10 is utilized in an insulin infusion delivery device used to deliver insulin to a human user or patient 24 via a subcutaneous cannula in fluidic communication with the outlet 20. The lower table included in FIG. 1 depicts information relevant to a low-dead volume version of the microfluidic circuit 10. The upper table depicts information relevant to a baseline version of the microfluidic circuit 10 upon which no volume reduction modifications have been made. The total volume of each flow component is depicted in FIG. 1 in Row A of both the upper and lower tables. The elastomer reservoir 12 supplies the downstream microfluidic circuit flow components with insulin until the elastomer no longer exerts sufficient pressure to overcome the flow resistance in the circuit 10. At that point, in this example, 87.39 µl of insulin remains in the reservoir 12. See Row D.

Row B in both the upper and lower tables depicts the flow rate Q through the various components. The flow rate Q is defined, at least in part, by flow restrictors and other components present within the circuit. Row C in both the upper and lower tables depicts the amount of time required for insulin to completely fill each dry flow component once flow from the reservoir 12 is initiated, as the sum of which is the total start-up time for the entire microfluidic circuit 10 to fill. This total start-up time reflects the time required to deliver a first dose of insulin to the user 24. Notably, the difference in volume between the standard pressure sensor (21.22 µl) and the low-dead volume pressure sensor (8.34 µl) contributes directly to the significant reduction in total start-up time of the circuit 10. Note that the fill time for the standard pressure sensor is over twice that of the low-dead volume fill time, while the total fill time of the standard circuit is over 1 hour and 15 minutes greater than the microfluidic circuit using low-dead volume components. This significant delay inherent in the baseline version of the circuit 10 is both an inconvenience and could be a risk to the user's health.

Row D in both the upper and lower tables depicts the amount of insulin that is effectively trapped within the microfluidic circuit 10 once the elastomer reservoir 12 can no longer induce flow at the outlet 20. Note that a significant portion of the trapped insulin, other than that remaining in the reservoir 12, is contained within the pressure sensor 16. Accordingly, use of a low-dead volume pressure sensor is advantageous to reduce the total amount of lost insulin within the microfluidic circuit 10.

The problems demonstrated by the baseline circuit are exacerbated as a microfluidic circuit increases in complexity. The addition of more elements critical to microfluidic circuit operation and patient safety (e.g., valves, pressure sensors, constant-volume chambers, variable-volume chambers, etc.) all increase the total dead volume of a system. Because these elements have a significantly larger total volume than the conduits or channels through which medication flows, their contribution to total system dead volume is substantial. The invention addresses this need, by providing structure and methods to reduce the dead volume of these flow components, to alleviate the problems of excess circuit fill time and trapped medication described above.

Figure 2:
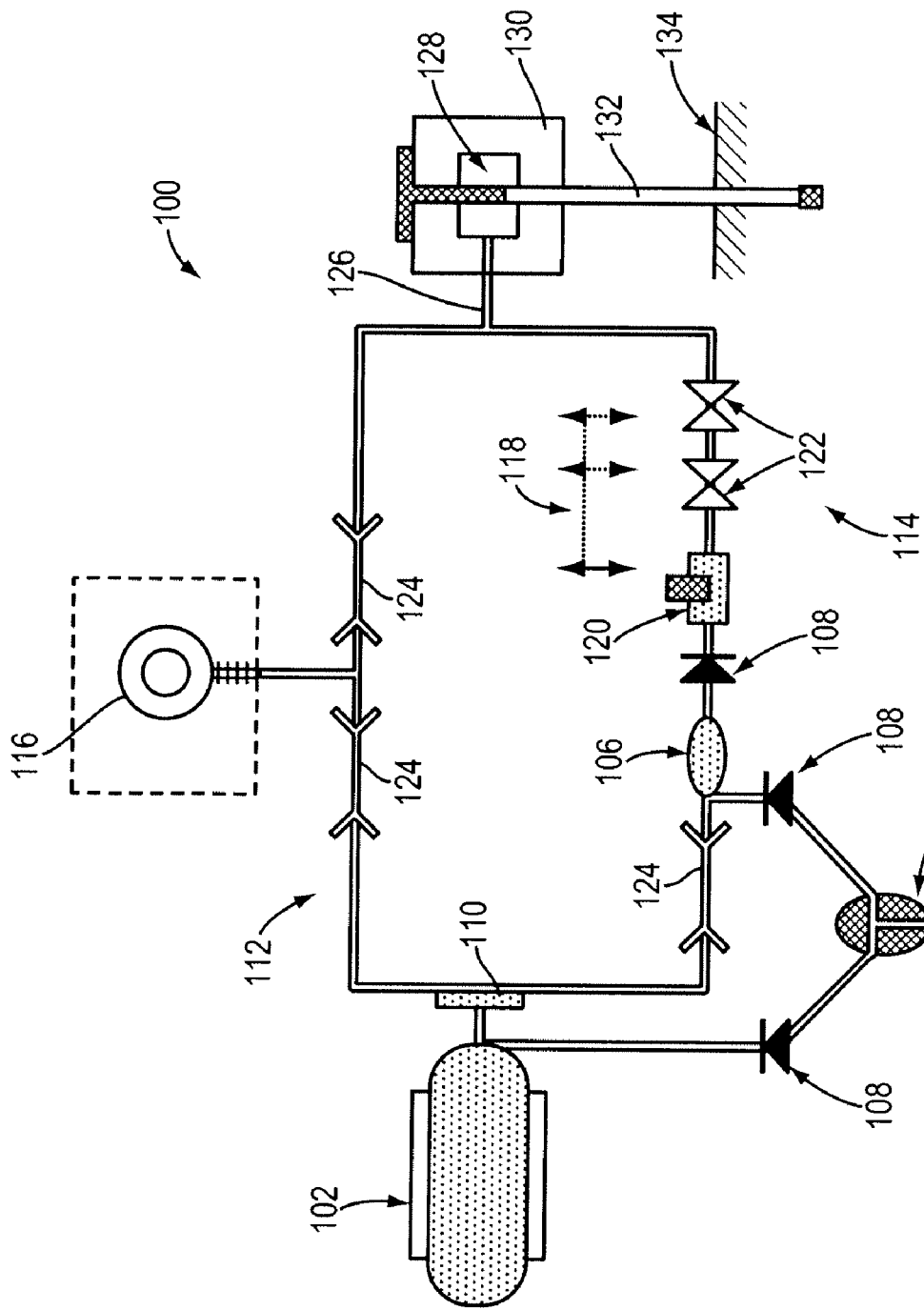
FIG. 2 is a schematic diagram of another exemplary infusion device microfluidic circuit in accordance with one embodiment of the invention.

FIG. 2 is a schematic diagram of an exemplary infusion device microfluidic circuit 100 that benefits from the low-dead volume technology described herein. Other infusion device microfluidic circuits benefit as well, such as those described, for example, in U.S. Patent Application Publication No. 2005/0165384 A1, published Jul. 28, 2005, the disclosure of which is hereby incorporated by reference herein in its entirety. Microfluidic circuits having other configurations or utilizing any number of other components also may benefit from the low-dead volume systems and methods described herein. The microfluidic circuit 100 includes a reservoir 102 that is, in this case, comprised of an elastomer bladder. A fill port 104 is used to introduce insulin to the microfluidic circuit 100. In this microfluidic circuit 100, introducing insulin via the fill port 104 fills both the reservoir 102 and a variable-volume bolus reservoir 106. Check valves 108 in the circuit 100 prevent backflow of insulin in a number of locations.

During use, insulin is forced from the reservoir 102 due to contraction of the elastomer bladder, through a filter 110, and into two parallel flowpaths: a basal flowpath 112 and a bolus flowpath 114. The basal flowpath 112 delivers a constant dose of insulin to a user; the bolus flowpath 114 delivers a bolus dose of insulin to the user as needed or desired by the user, upon actuation of a bolus button 118. The basal flowpath 112 includes a pressure sensor 116 or other flow sensor in communication with the flowpath 112. To deliver a bolus via the bolus flowpath 114, the user presses the bolus button 118 that drives a single stroke (delivering a single dose) of a bolus displacement chamber 120 and opens two valves 122. The valves 122 are in series providing failsafe redundancy for safety purposes. Flow restrictors 124 limit the rate of fluid flow through the flowpaths 112, 114. The parallel flowpaths 112, 114 join at a common channel 126, upstream of an internal chamber or a cannula void 128. The cannula void 128 is formed in a cannula base 130, that provides a fluidic connection to a cannula 132. The cannula 132 extends below the skin 134 of the user, thus delivering the insulin subcutaneously. In the depicted microfluidic circuit 100, reducing the dead volume in any or all of the variable-volume bolus reservoir 106, the valves 122, the pressure sensor 116, and the cannula void 128 decreases the dead volume throughout the entire microfluidic circuit 100.

Figure 3:
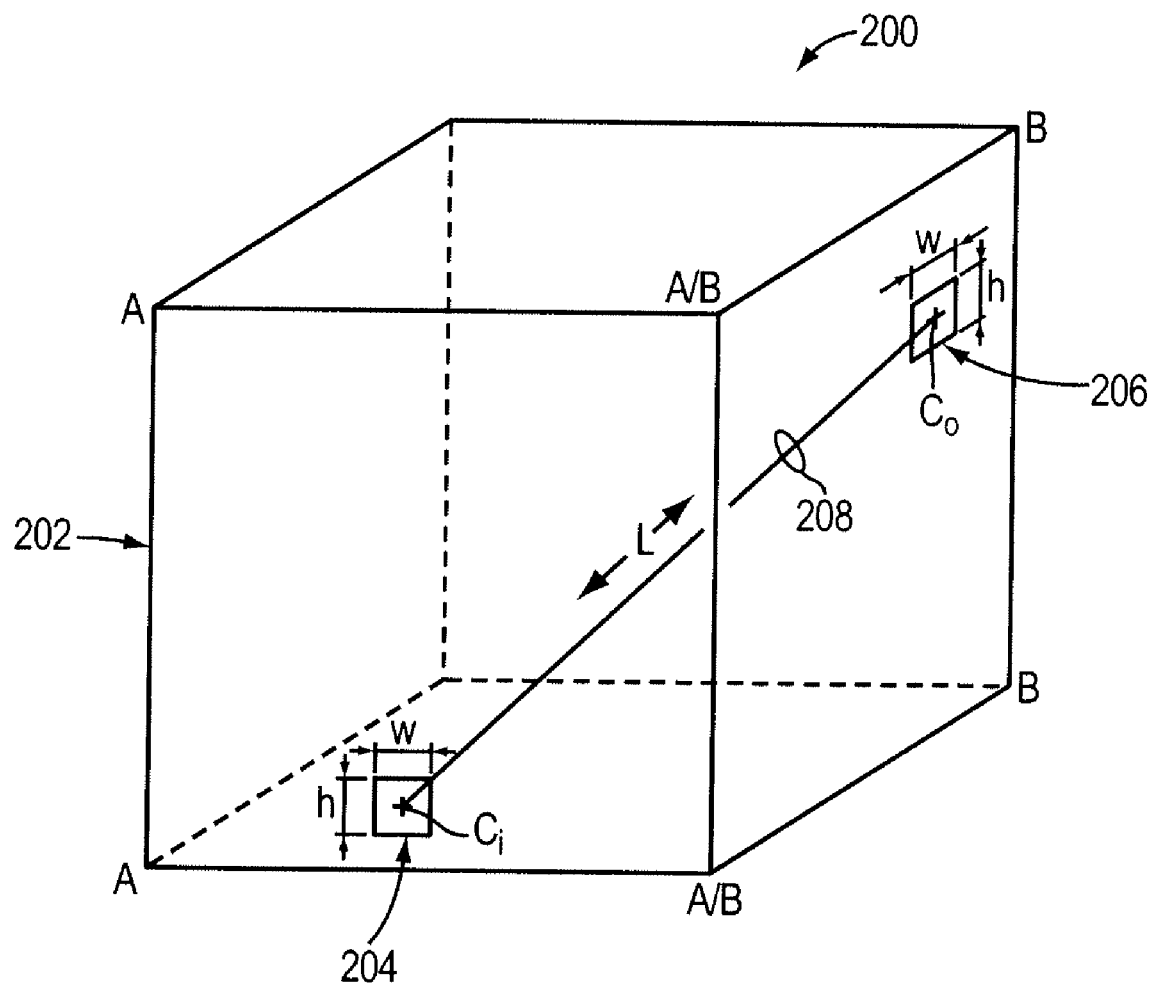
FIG. 3 is a schematic diagram of a theoretical microfluidic circuit flow component.

FIG. 3 depicts a theoretical flow component 200. While most flow components utilized in a microfluidic circuit serve specific purposes, each generally share several common elements, as depicted in FIG. 3. First, the flow component includes a housing or some other inner physical boundary that is in contact with the fluid passing therethrough. In FIG. 3, this inner physical boundary 202 is depicted as a hollow cube. Second, the flow component includes an inlet, through which fluid flows into the component. In FIG. 3, the inlet 204 penetrates a wall of the physical boundary 202 defined by corners bearing the letter "A"; the dimensions of the inlet 204 are defined by a height h, and a width w, although the inlet 204 could be circular or any other shape. Third, the flow component includes an outlet, through which fluid flows out of the component. In FIG. 3, the outlet 206 penetrates a wall of the physical boundary 202 defined by the corners bearing the letter "B"; the dimensions of the outlet 206 are defined by a height h, and a width w, in this case, matching the dimensions of the inlet 204, although the outlet 206 could be any shape or size and disposed at any location along the boundary 202.

The inner physical boundary of a flow component defines three volumes: a total volume V, a working volume W, and a dead volume D. The total volume V is the volume bounded by the inner physical boundary; accordingly, in FIG. 3, the total volume V is defined by the walls of the cube (i.e., the inner physical boundary 202). The working volume W is the minimum volume required to perform the function of the flow component, including connecting fluidicly the inlet and the outlet. In FIG. 3, assume that the theoretical flow component 200 functions as a constant-volume chamber through which fluid passes (where the entire cube must be filled with fluid via the inlet 204 prior to any fluid exiting the cube via the outlet 206). The working volume W is the volume defined around a straight line 208 from a center $C_i$ of the inlet 204 to a center $C_o$ of the outlet 206, the straight line having a length L. The actual volume of this working volume W may be defined, in part, by the total length of straight line L and the height h and width w of the inlet 204 and the outlet 206, assuming the working volume has outer dimensions substantially similar to height h and width w. Therefore the working volume W may be defined approximately by equation (i) below.

$$W = h \times w \times L \quad \text{(i)}$$

The dead volume D is the volume of the flow component 200 unnecessary to perform the function, and may be defined as the difference between the total volume V and the working volume W (in this case, the remainder of the volume contained within the inner physical boundary 202, not including the working volume W), as shown in equation (ii) below.

$$D = V - W \quad \text{(ii)}$$

By reducing the dead volume D of a flow component, the dead volume of a microfluidic circuit may be decreased, approaching, ideally, a condition where the total volume of the low-dead volume component $V_{LD}$ equals the working volume W of a standard-dead volume flow component, i.e., $V_{LD} = W$.

Different implementations may be utilized to decrease the dead volume of various flow components. In general, however, the various dead volume-reduction examples described herein may effectively configure the flow component to reduce the dead volume, such that the working volume is substantially the same as the total volume or as close to the total volume as reasonably achievable, under the circumstances. Regardless of the configuration changes implemented, a number of factors may be considered. For example, the function and operational performance of the flow component should not be affected adversely by the dead volume-reduction configuration change. The dead volume-reduction change should consider the potential impact on pressure losses associated with the flow component. Care should be taken when reducing dead volume of a flow component, to ensure the component can still be manufactured at acceptable cost. Four examples of the use of dead volume-reduction configuration changes to reduce the dead volume of four flow components are described below.

Example 1

Figure 4A:
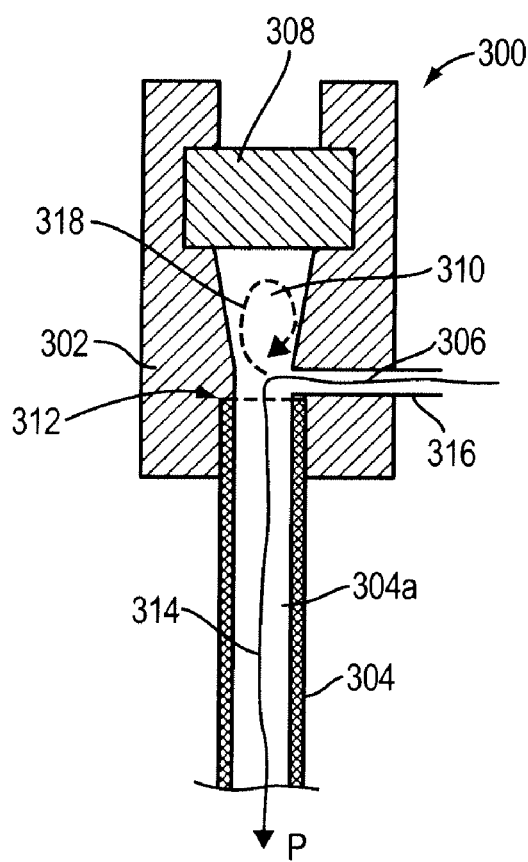
FIGS. 4A and 4B are schematic sectional views of an exemplary cannula base and a low-dead volume version of the same cannula base in accordance with one embodiment of the invention.

FIG. 4A is a schematic sectional view of a cannula base 300. The base includes a housing 302 connected to a cannula 304. The cannula base 300 allows for fluidic communication between a reservoir of a microfluidic circuit (not shown) and a patient, via an chamber inlet 306. In general, a needle (not shown) penetrates a septum 308 and passes through an internal chamber 310 defined by the housing 302. The internal chamber 310 functions as a constant volume chamber through which insulin flows during use of a device containing the microfluidic circuit; a chamber outlet 312 is depicted with a dashed line in FIG. 4A. After passing through the internal chamber 310, the needle passes through a lumen 304a formed by the cannula 304. The rigidity of the needle allows the cannula 304 to be more easily inserted into a patient P. Once the cannula 304 is inserted, the needle is removed from the housing 302, thereby creating a direct flow path 314 from the reservoir, through a channel 316, into the inlet 306, through the internal chamber 310, out of the outlet 312, and into the patient P, via the lumen 304a. The septum 308 can be of the self-sealing variety. This direct flow path 314 is the working volume W of the internal chamber (i.e., the minimum volume required for the flow component to perform its function). During use, however, the insulin moving along the direct flow path 314 fills the internal chamber 310. As can be seen in FIG. 4A, diversionary flow 318 fills the dead volume within the internal chamber 310 with insulin, resulting in wasted insulin and increased fill time.

Figure 4B:
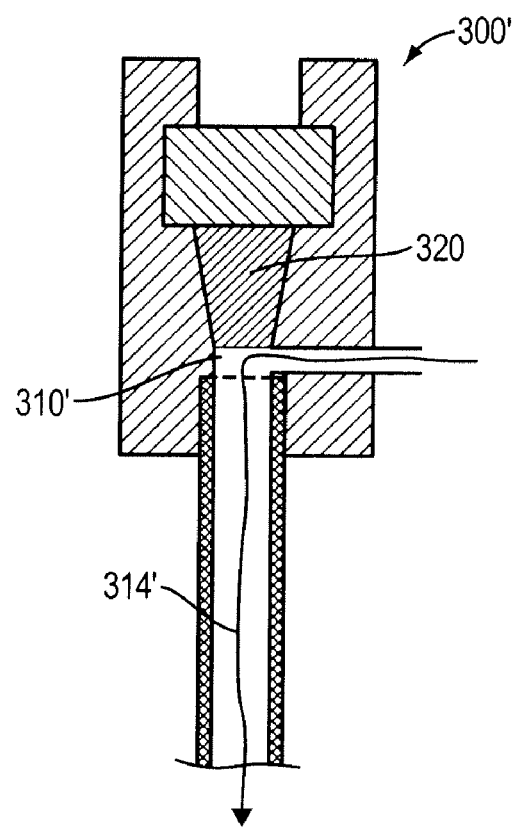

Depicted in FIG. 4B is a cannula base 300' according to one embodiment of the present invention present invention with reduced dead volume. In this embodiment, a volume reduction element, such as secondary septum or plug 320 is used to reduce the dead volume within the internal chamber 310. This forms a reduced volume flowpath 314'. The remaining total volume of the internal chamber 310' (that will be filled with insulin) is significantly reduced and approaches the working volume. In this embodiment, the plug 320 is depicted as discrete from the septum 308; however, other embodiments may integrate the septum 308 and plug 320 into a single element.

In one embodiment, the cannula base 300 depicted in FIG. 4A includes a total volume V of 1.74 μl. Of this amount, 1.5 μl was determined to be dead volume D and was subsequently reduced by plug 320, leaving a working volume W of 0.24 μl. For this embodiment, then, reducing the dead volume D results in a working volume W that is about 13.8% of the total volume V for the cannula base 300' of FIG. 4B, thus achieving a 86.2% reduction in the volume of the cannula base 300. Other reductions are also contemplated.

Example 2

Figure 5A:
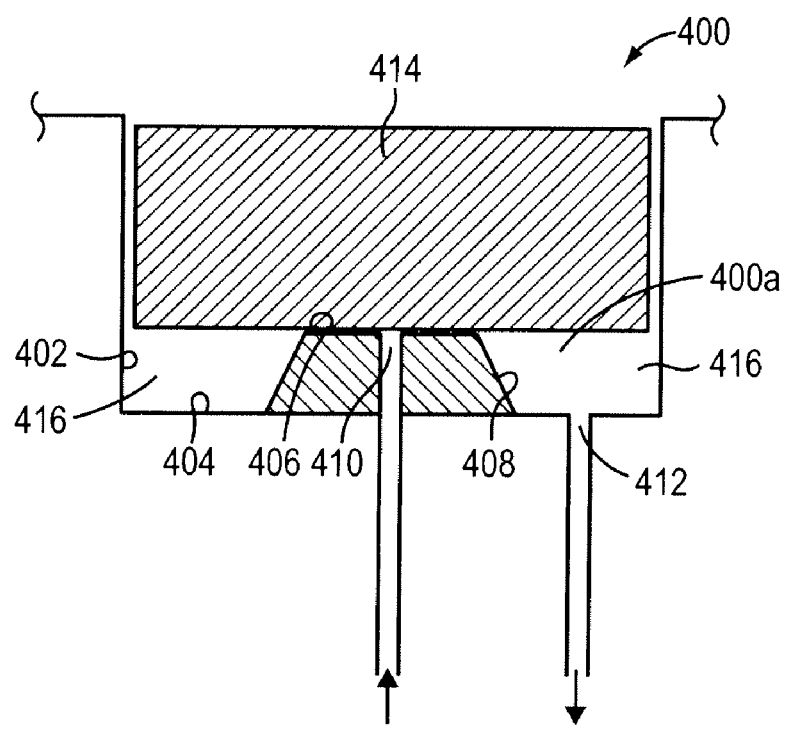
FIGS. 5A and 5B are schematic sectional views of an exemplary valve and a low-dead volume version of the same valve in accordance with one embodiment of the invention.

FIG. 5A is a schematic sectional view of a valve 400. This particular type of valve is often referred to as a volcano valve. The valve 400 includes a valve housing wall 402 and a valve housing base 404. The wall 402 and the base 404 at least partially define a valve chamber 400a. Centrally located on the base 404 is a raised plateau 406 having a tapered, frustoconical configuration 408. A valve inlet 410 penetrates the plateau 406, while a valve outlet 412 penetrates the base 404. A sealing member 414 corresponding generally to the wall 402 is pressed against the plateau 406 to seal the inlet 410, thus stopping a flow of fluid into the valve 400. In this case, the plateau 406 functions as a valve seat. The elevation of the raised plateau 406 helps ensure a positive seal between the sealing member 414 and the plateau 406. Due to the elevation of the raised plateau 406 over the base 404, however, an annular void 416 is formed between the sealing member 414 and the base 404. This void 416 creates significant dead volume in the valve 400.

Figure 5B:
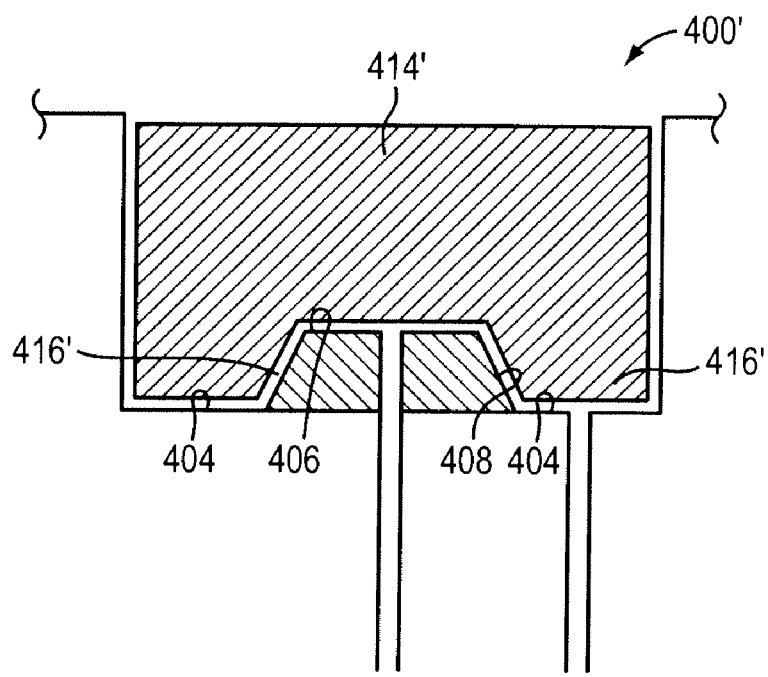

Depicted in FIG. 5B is a valve 400' according to one embodiment of the present invention with reduced dead volume. In this embodiment, the dimensions and configuration of the sealing member 414' have been modified with a matching frustoconical recess to reduce dead volume within the valve 400'. The sealing member 414' contacts the raised plateau 406 to ensure a proper seal as does the valve 400. However, instead of having a flat underside, as depicted in FIG. 5A, the sealing member 414' is a volume reduction element, configured to more closely match the frustoconical configuration 408 and the base 404 of the valve 400'. To ensure that the valve 400' closes properly, the dimensions of the sealing member 414' should be such that the sealing member 404 positively contacts the plateau 406. In an alternative embodiment, the base 404 may function as a volume reduction element, by configuring the base such that the distance between the top of the plateau 406 and the base 404 is reduced. Thus, modifying the dimensions of the sealing member 414' and/or the base 404 reduces the size of the void 416' and, accordingly, the dead volume of the valve 400'.

In one embodiment, the valve 400 depicted in FIG. 5A includes a total volume V of 1.15 µl. Of this amount, 1.15 µl was determined to be dead volume D and was subsequently reduced by modifications to sealing member 414', leaving a working volume W of 0.0 µl. For this embodiment, then, reducing the dead volume D results in a working volume W that is about 0% of the total volume V for the valve 400' of FIG. 5B, thus achieving a 100% reduction in the volume of the valve 400. Other reductions are also contemplated.

Example 3

Figure 6A:
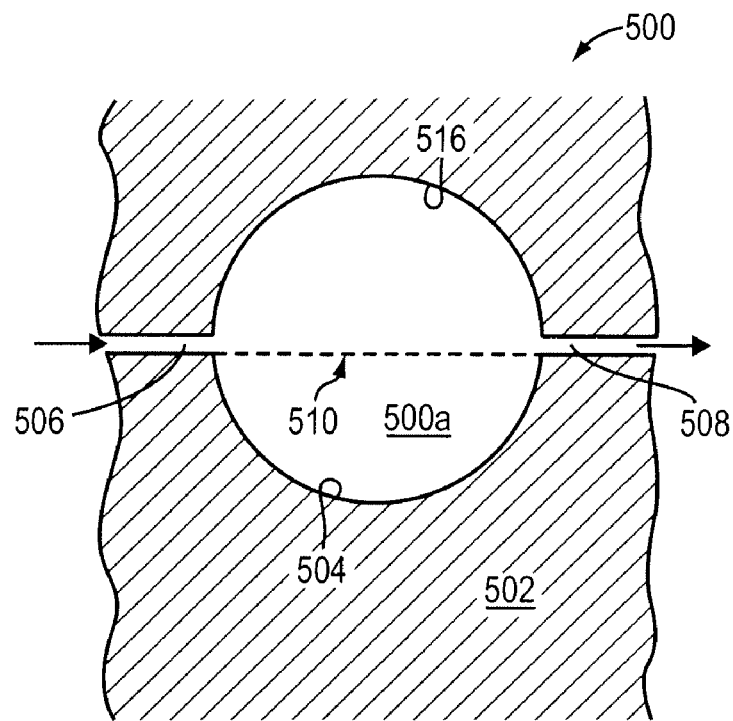
FIGS. 6A and 6B are schematic sectional views of an exemplary variable-volume chamber and a low-dead volume version of the same variable-volume chamber in accordance with one embodiment of the invention.

FIG. 6A is a schematic sectional view of a variable-volume chamber 500. The chamber 500 is formed within a solid housing 502 and has a rigid base surface 504, as well as an inlet 506, and an outlet 508. A rigid top surface 516 defines the upper surface of the chamber 500. As can be seen in FIG. 6A, the entire volume of an internal chamber 500a below a line 510a must be filled before any fluid may pass out of the outlet 508.

Figure 6B:
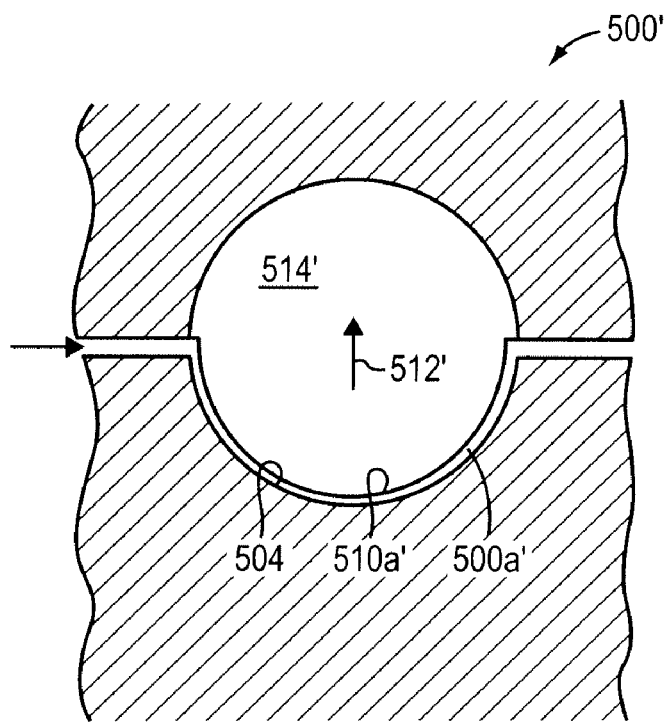

Depicted in FIG. 6B is a variable-volume chamber 500' according to one embodiment of the present invention with reduced dead volume. In this case, membrane 510' is biased or disposed against the rigid base 504 of the internal chamber 500a' to define a first small volume approaching zero, as depicted here. As fluid enters the internal chamber 500a', the membrane 510a' expands 512'. The pressure contained within expansion volume 514' is immediately exerted against the membrane 510a' and the fluid contained within the internal chamber 500a'. Pressure within the expansion volume 514' may be relieved by a suitable vent, not shown. Due to the initial location of the membrane 510a', once filling begins, pressure is essentially immediately exerted against the fluid, without requiring filling of an excessive dead volume of the internal chamber 500a'.

In one embodiment, the variable-volume chamber 500 depicted in FIG. 6A includes a total volume V of 230 µl. Of this amount, 218.5 µl was determined to be dead volume D and was subsequently reduced by membrane 510a', leaving a working volume W of 11.5 µl. For this embodiment, then, reducing the dead volume D results in a working volume W that is about 5% of the total volume V for the variable-volume chamber 500' of FIG. 6B, thus achieving a 95% reduction in the volume of the variable-volume chamber 500. Other reductions are also contemplated.

Example 4

FIG. 7A is a schematic top view of a pressure sensor 600; FIG. 8A depicts a schematic sectional view of the pressure sensor 600 taken along line 8A-8A. The pressure sensor 600 is formed within a solid housing 602 and has a rigid base 604 and a rigid wall 606 as well as an inlet 608, and an outlet 610. A flexible membrane 612 forms the top boundary of a pressure chamber 614. The total volume of the flow component is therefore defined at least in part by the base 604, the wall 606, and the membrane 612. Generally, above the membrane 612 is some type of pressure-sensitive element (not shown) to detect deflection of the membrane 612 caused by a change in the pressure within the chamber 614. As can be understood from the figures, the entire volume of the pressure chamber 614 must be filled before the fluid contacts the membrane 612.

Depicted in FIG. 7B is a schematic top view of a pressure sensor 600' according to one embodiment of the present invention with reduced dead volume; FIG. 8B depicts a schematic sectional view of the pressure sensor 600' taken along line 8B-8B. One or more raised structures or plateaus 616 fill a significant portion of the pressure chamber 614', thereby reducing the dead volume. The plateaus each include at least a side surface 616a and a top surface 616b. The top surface 616b of the raised plateau 616 lies proximate and just slightly below the membrane 612, to allow the fluid contained within pressure chamber 614' to contact the entire surface of the membrane 612, ensuring accurate pressure readings. Thus, the total volume of the chamber 614' is now significantly closer to the working volume, which is defined at least in part by the base 604, membrane 612, the side surfaces 616a, and the top surfaces 616b.

In one embodiment, the pressure sensor 600 depicted in FIGS. 7A and 8A includes a total volume V of 21.22 µl. Of this amount, 12.88 µl was determined to be dead volume D and was subsequently reduced by plateau 616, leaving a working volume W of 8.34 µl. For this embodiment, then, reducing the dead volume D results in a working volume W that is about 39.3% of the total volume V for the pressure sensor 600' of FIGS. 7B and 8B, thus achieving a 60.7% reduction in the volume of the pressure sensor 600. Other reductions are also contemplated.

Application of the low-dead volume techniques described herein can significantly reduce dead volume of a microcircuit 100 such as that depicted in FIG. 2. As depicted in FIG. 2, the basal circuit 112 includes a pressure sensor 116 and a cannula void 128. The bolus circuit 114 includes a variable-volume chamber 106 and two valves 122. The total volume of all conduits in the microcircuit 100 is about 7 µl, of which nearly none is dead volume. TABLE 1, below, depicts relevant properties of exemplary flow components in an exemplary microcircuit, as those components are described in Examples 1-4.

Assuming a microcircuit 100, such as that depicted in FIG. 2, the difference in volume of a standard microcircuit (having baseline-volume components) versus the volume of a low-dead volume circuit (having low-dead volume components) is depicted.

TABLE 1

Reduction in Dead Volume for Flow Components

| Example | Component | V (µl) | D (µl) | W (µl) | Improvement (% Reduction In V) |
|---|---|---|---|---|---|
| 1 | Cannula Void 128 | 1.74 | 1.5 | .24 | 86.2 |
| 2a | Valve 122 | 1.15 | 1.15 | 0 | 100 |
| 2b | Valve 122 | 1.15 | 1.15 | 0 | 100 |
| 3 | Bolus Reservoir 106 | 230 | 218.5 | 11.5 | 95 |
| 4 | Pressure Sensor 116 | 21.22 | 12.88 | 8.43 | 60.3 |
| All Conduits | — | 7 | 0 | 7 | 0 |
| Total | Microcircuit 100 | 262.26 | 235.18 | 27.08 | 89.7 |

TABLE 2, below, depicts other relevant properties of exemplary flow components in an exemplary microcircuit, as those components are described in Examples 1-4. For each Example, the total volume V and dead volume D of a standard flow component is provided. After utilizing the low-dead volume structures described herein, dead volume D of each component was essentially eliminated, to achieve the significantly smaller, essentially idealized, working volume W. Also provided is the cumulative volume for all conduits within the microcircuit. These representative conduits do not contain any dead volume.

Flow rates Q through each component are also provided. The flow rates Q are used to calculate the fill time for each component. Initially, fill times for the exemplary components 1-4 are calculated before any dead-volume reduction structures are utilized. In that case, total volume V is divided by the flow rate Q to obtain the fill time for that component. Next, fill times for the exemplary components 1-4 are calculated after dead-volume reduction structures (as described in Examples 1-4, above) are utilized. In that case, working volume W is divided by the flow rate Q to obtain the fill time for the low-dead volume component. It should be noted that, with regard to Example 3, the variable-volume chamber, the working volume is, as defined above, the minimum volume required to perform the function of the flow component. Since the function of the chamber is to hold liquid medicine, it has been assumed here for the purposes of illustration of the concept that a minimum of 11.5 µl is required for the functional working volume. Indeed, the working volume and dead volume of the variable-volume chamber may change as the chamber is made to hold different amounts of liquid medicine.

Reduction in fill times from that of the standard baseline component to that of the low-dead volume component are also provided. These reductions range from about 0.115 hr (6 min., 54 sec.) for Example 1 to about 1.279 hr (1 hr., 16 min., 44 sec.) for Example 4. As noted above, while the reduction in fill time for Example 3 is quite large, this reduction varies depending on the working volume W selected. Regardless, the total reduction in fill time for the complete circuit is significant.

TABLE 2

Reduction in Fill Time for Flow Components

| Example | V (µl) | D (µl) | W (µl) | Flow Rate Q (µl/hr) | Fill Time V at Q (hr) | Fill Time W at Q (hr) | Fill Time Reduc. (hr) | Improvement (% Reduc.) |
|---|---|---|---|---|---|---|---|---|
| 1 | 1.74 | 1.5 | .24 | 5 | 0.348 | 0.048 | 0.3 | 86.2 |
| 2a | 1.15 | 1.15 | 0 | 10 | 0.115 | 0 | 0.115 | 100 |
| 2b | 1.15 | 1.15 | 0 | 10 | 0.115 | 0 | 0.115 | 100 |
| 3 | 230 | 218.5 | 11.5 | 10 | 23 | 1.15 | 21.85 | 95 |
| 4 | 21.22 | 12.88 | 8.34 | 10 | 2.122 | 0.834 | 1.288 | 60.7 |
| All Conduits | 7 | 0 | 7 | 185 | 0.038 | 0.038 | 0 | 0 |
| Total | 262.26 | 245.53 | 15.67 | N/A | 25.738 | 2.07 | 23.668 | 91.9 |

The various materials utilized in the flow components described herein, as well as the microfluidic circuits in which those flow components are utilized, may be metal, glass, and/or any type of polymer suitable for sterilization and useful for delivering insulin or other medicaments subcutaneously. Polyurethane, polypropylene, PVC, PVDC, EVA, and others are contemplated for use. More specifically, medical-grade plastics may be utilized for the cannula itself, as well as other components that contact or otherwise penetrate the body of the patient. Needles made from medical-grade stainless steel are also desirable, to prevent failure associated with use. Accordingly, the components utilized to reduce the dead volume within the various components should be the same as, similar to, or at least compatible with the existing materials utilized.

While there have been described herein what are to be considered exemplary and preferred embodiments of the present invention, other modifications of the invention will become apparent to those skilled in the art from the teachings herein. The particular methods of manufacture and geometries disclosed herein are exemplary in nature and are not to be considered limiting. It is therefore desired to be secured in the appended claims all such modifications as fall within the spirit and scope of the invention. Accordingly, what is desired to be secured by Letters Patent is the invention as defined and differentiated in the following claims, and all equivalents.

What is claimed is:

1. A method for reducing a dead volume of a microfluidic circuit comprising a reservoir, an outlet, and a microfluidic flowpath fluidly connecting the reservoir and the outlet, the method comprising:
providing a microfluidic flow component located between the reservoir and the outlet for performing a function and in fluidic communication with the microfluidic flowpath,
wherein the microfluidic flow component comprises a total volume comprising a working volume and a dead volume, wherein the working volume comprises a volume necessary for the microfluidic flow component to perform the function and the dead volume comprises a volume unnecessary for the microfluidic flow component to perform the function; and
configuring at least one of the reservoir, the microfluidic flowpath, and the microfluidic flow component to reduce the dead volume, such that the working volume is substantially the same as the total volume.

2. The method of claim 1, wherein the configuring step results in the total volume being substantially the same as the working volume.

3. The method of claim 1, wherein the microfluidic flow component comprises at least one of a flowpath transition, a valve, a constant-volume fluid chamber, a pressure sensor, and a variable-volume fluid chamber.

4. The method of claim 3, wherein the microfluidic flow component comprises a constant-volume fluid chamber defining an internal chamber, a chamber inlet in fluidic communication with the internal chamber, and a chamber outlet in fluidic communication with the internal chamber, wherein the internal chamber comprises the total volume, and wherein the configuring step comprises:
providing a volume reduction element within the internal chamber so as to define a reduced volume flow path from the chamber inlet to the chamber outlet, wherein the reduced volume flow path substantially defines the working volume.

5. The method of claim 4, wherein the working volume comprises about 14% of the total volume prior to the configuring step.

6. The method of claim 3 wherein the microfluidic flow component comprises a valve, the valve comprising a housing defining a valve chamber therein, the valve chamber defined at least in part by a sidewall and a valve seat, the valve seat comprising at least one of a base surface and a raised plateau defining a valve inlet and a plateau wall extending from the raised plateau to the base surface, the base surface defining a valve outlet, and a seal member having a surface corresponding substantially to the sidewall and the raised plateau, and wherein the configuring step comprises:
providing a volume reduction element within the valve chamber such that the seal member corresponds substantially to the base surface and the plateau wall.

7. The method of claim 6, wherein the working volume comprises about 0% of the total volume prior to the configuring step.

8. The method of claim 3 wherein the microfluidic flow component comprises a pressure sensor comprising a flexible membrane and a base surface disposed in opposition to the flexible membrane, wherein a volume located between the flexible membrane and the base surface defines the total volume, and wherein the configuring step comprises:
providing two raised structures disposed between the flexible membrane and the base surface, wherein top surfaces of the raised structures are proximate to, but not in contact with, the flexible membrane, wherein the side surfaces of the raised structures intersect the base surface, and wherein the side surfaces of the raised structures, the base surface, and the flexible membrane at least partially define a flow channel, and wherein the flow channel defines the working volume.

9. The method of claim 8, wherein the working volume comprises about 40% of the total volume prior to the configuring step.

10. The method of claim 3, wherein the variable-volume fluid chamber comprises a base surface, an inlet, and a separate outlet, and wherein the configuring step comprises:
providing a flexible membrane wherein the base surface and the membrane define a first volume when the membrane is proximate the base surface, wherein the base surface and the membrane define a second volume when the membrane is displaced by a fluid pressure away from the base surface, and wherein the membrane is biased towards the base surface.

11. The method of claim 10, wherein the working volume comprises about 5% of the total volume prior to the configuring step.

* * * * *